United States Patent [19]
Atkinson et al.

[11] Patent Number: 5,849,943
[45] Date of Patent: Dec. 15, 1998

[54] STILBENE DERIVATIVES USEFUL AS CYCLOOXYGENASE-2 INHIBITORS

[75] Inventors: Joseph Atkinson; Zhaoyin Wang, both of Kirkland, Canada

[73] Assignee: Merck Frosst Canada, Inc., Kirkland, Canada

[21] Appl. No.: 817,128

[22] PCT Filed: Oct. 24, 1995

[86] PCT No.: PCT/CA95/00601

§ 371 Date: Apr. 7, 1997

§ 102(e) Date: Apr. 7, 1997

[87] PCT Pub. No.: WO96/13483

PCT Pub. Date: May 9, 1996

[51] Int. Cl.$^6$ ................................................. C07C 69/76
[52] U.S. Cl. ..................... 560/8; 560/17; 514/532; 514/533; 514/534; 514/539
[58] Field of Search .................... 514/532, 533, 514/534, 539; 560/8, 17

[56] References Cited

U.S. PATENT DOCUMENTS

| | | | |
|---|---|---|---|
| 5,082,974 | 1/1992 | Hashimoto et al. | 568/41 |
| 5,344,991 | 9/1994 | Reitz et al. | 568/34 |
| 5,393,790 | 2/1995 | Reitz et al. | 514/709 |
| 5,474,995 | 12/1995 | Ducharme et al. | 514/241 |

FOREIGN PATENT DOCUMENTS

| | | |
|---|---|---|
| WO 95/00501 | 1/1995 | Canada . |
| 424541 | 5/1991 | Japan . |

OTHER PUBLICATIONS

Toda et al., "A New Preparative Method for (E)-2, 3-Diarylbut-2-enedials", Journal of the Chemical Society, Chemical Communications, No. 18, Sep. 1984, pp. 1234–1235.

Tsuji et al., "Organic Synthesis by means of noble metal compounds. XXI. Palladium–catalyzed carbonylation of diphenylacetylene", Journal of the American Chemical Society, vol. 88, No. 6, Mar. 20, 1966, pp. 1289–1292.

Dhawan et al., "Preparation of Benzocyclobutenols from o–halostyrene oxides", vol. 45, No. 5, 29 Feb. 1980, pp. 922–924.

*Primary Examiner*—Raymond Henley, III
*Assistant Examiner*—Dwayne C. Jones
*Attorney, Agent, or Firm*—Richard C. Billups; Curtis C. Panzer; David L. Rose

[57] ABSTRACT

The invention encompasses novel compounds of Formula I useful in the treatment of cyclooxygenase-2 mediated diseases.

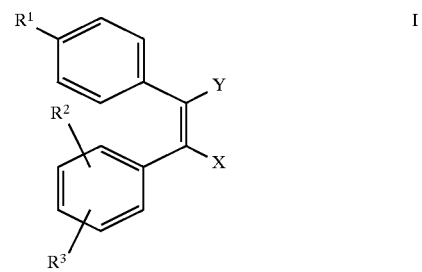

The invention also encompasses certain pharmaceutical compositions and methods for treatment of cyclooxygenase-2 mediated diseases comprising the use of compounds of Formula I.

17 Claims, No Drawings

STILBENE DERIVATIVES USEFUL AS CYCLOOXYGENASE-2 INHIBITORS

CROSS REFERENCE TO RELATED APPLICATIONS

This application is a U.S. National Phase application based upon PCT Application No. CA95/00601 filed on Oct. 24, 1995, copending therewith, which was based upon U.S. Application No. 08/330,172 filed Oct. 27, 1994, copending therewith, abandoned on Oct. 27, 1994, priority of which is claimed hereunder.

BACKGROUND OF THE INVENTION

This invention relates to compounds and pharmaceutical compositions for the treatment of cyclooxygenase mediated diseases and methods of treatment thereof.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

A number of stilbene derivatives are known in the chemical literature. Toda et al., in Chem. Commun. 1234–5 (1984) describe the dialdehydes A and the diol B is described by Tsuji et al, J. Am. Chem. Soc. 88, 1289–92 (1966), and diol C was prepared by Dhawau et al., J. Org. Chem., 45, 922–4 (1980). No utility is disclosed for these compounds, nor do they carry the $R^1$ substituent of the present invention.

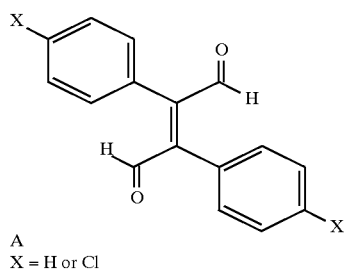

A
X = H or Cl

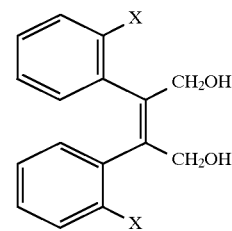

B X = H Tsuji
C X = Cl Dhawan

Structure D is disclosed as having usefulness for treating hyperlipidemia by Hashimoto et al, European Patent Application 424,541 (May 2, 1991).

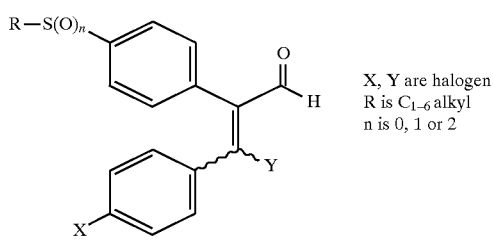

D
X, Y are halogen
R is $C_{1-6}$ alkyl
n is 0, 1 or 2

These compounds (D) lack the second carbon substituent X of the present invention and have an unrelated utility.

SUMMARY OF THE INVENTION

The invention encompasses novel compounds of Formula I useful in the treatment of cyclooxygenase-2 mediated diseases.

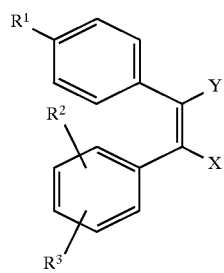

I

The invention also encompasses certain pharmaceutical compositions and methods for treatment of cyclooxygenase-2 mediated diseases comprising the use of compounds of Formula I.

DETAILED DESCRIPTION OF THE INVENTION

The invention encompasses the novel compound of Formula I useful in the treatment of cyclooxygenase-2 mediated diseases

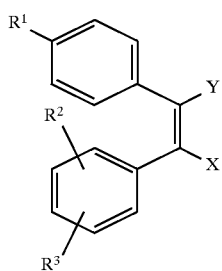

or pharmaceutically acceptable salts thereof wherein
X is
(a) $CH_2OH$
(b) CHO, or
(c) $CO_2R^4$,
Y is
(a) $CH_2OH$, or
(b) $CH_2OCOR^5$,
$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$;
$R^2$ and $R^3$ each are independently selected from the group consisting of
(a) hydrogen,
(b) halo,
(c) $C_{1-6}$alkoxy,
(d) $C_{1-6}$alkylthio,
(e) CN,
(f) $CF_3$,
(g) $C_{1-6}$alkyl,
(h) $N_3$;
$R^4$ is selected from the group consisting of
(a) hydrogen, and
(b) $C_{1-6}$alkyl;
$R^5$ is selected from the group consisting of
(a) hydrogen,
(b) $C_{1-6}$alkyl,
(c) mono- or disubstituted phenyl wherein the substituent is selected from
(1) hydrogen,
(2) halo,
(3) $C_{1-6}$alkyl,
(4) $C_{1-6}$alkoxy,
(5) $C_{1-6}$alkylthio,
(6) OH,
(7) CN,
(8) $CF_3$,
(9) $CO_2R^4$.

A preferred genus of compounds of Formula I is that wherein:
Y is $CH_2OH$ or $CH_2OCOR^5$;
$R^1$ is selected from the group consisting of
(a) $S(O)_2CH_3$,
(b) $S(O)_2NH_2$,
(c) $S(O)_2NHC(O)CF_3$,
(d) $S(O)NHCH_3$,
(e) $S(O)NHNH_2$, and
(f) $S(O)NHNHC(O)CF_3$;
$R^2$ and $R^3$ are each independently selected from the group consisting of
(a) hydrogen,
(b) fluoro, chloro, and bromo,
(c) $C_{1-4}$alkoxy,
(d) $C_{1-4}$alkylthio,
(e) CN,
(f) $CF_3$,
(g) $C_{1-4}$alkyl, and
(h) $N_3$.

Within this sub-genus is the class of compounds of Formula I wherein:
$R^2$ and $R^3$ are each independently selected from the group consisting of
(1) hydrogen, and
(2) halo;
$R^4$ is hydrogen; and
$R^5$ is $C_{1-6}$alkyl.

This group may be more particularly defined as the compounds of Formula I wherein
$R^1$ is selected from the group consisting of
(a) $S(O)_2CH_3$, and
(b) $S(O)_2NH_2$;
$R^2$ and $R^3$ are each independently selected from the group consisting of
(1) hydrogen,
(2) halo, selected from the group consisting of fluoro, chloro and bromo.

Another preferred genus of compounds of Formula I is that wherein:
X is $CO_2R^4$,
Y is $CH_2OCOR^5$,
$R^1$ is $S(O)_2CH_3$,
$R^2$ and $R^3$ each are independently selected from the group consisting of
(a) hydrogen, and
(b) halo,
$R^4$ is selected from the group consisting of
(a) hydrogen, and
(b) $C_{1-6}$alkyl,
$R^5$ is selected from the group consisting of
(a) $C_{1-6}$alkyl,
(b) mono- or disubstituted phenyl wherein the substituent is selected from
(1) hydrogen,
(2) halo,
(3) $C_{1-6}$alkoxy, and
(4) OH.

For purposes of this specification alkyl is defined to include linear, branched, and cyclic structures, with $C_{1-6}$alkyl including including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies -$SCH_2CH_2CH_3$.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of Formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of Formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of Formula I may also be useful for the treatment of dementia including pre-senile and senile dementia, and in particular, dementia associated with Alzheimer Disease (i.e. Alzheimer's dementia).

Compounds of Formula I will also inhibit prostanoid-induced smooth muscle contraction by preventing the synthesis of contractile prostanoids and hence may be of use in the treatment of dysmenorrhea, premature labor and asthma. They will also be useful to inhibit bone loss (osteoporosis).

By virtue of its high cyclooxygenase-2 (COX-2) activity and/or its selectivity for cyclooxygenase-2 over cyclooxygenase-1 (COX-1) as defined above, compounds of Formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptible to NSAID induced asthma.

Similarly, compounds of Formula I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase1 or cyclooxygenase-2 and a compound of Formula I. The $IC_{50}$ values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 $IC_{50}$ of 1 nM to 1 $\mu$M. By way of comparison, Ibuprofen has an $IC_{50}$ for COX-2 of 1 $\mu$M, and Indomethacin has an $IC_{50}$ for COX-2 of approximately 100 nM. For the treatment of any of these cyclooxygenase mediated diseases, compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of the present invention can be prepared according to the following methods.

Method A:

A diphenyl lactone 2 is reduced to the diol 1a by a suitable reducing agent such as diisobutyl aluminum hydride or lithium aluminum hydride in an appropriate solvent such as toluene, hexane, tetrahydrofuran or ether. The diol is acylated with an anhydride or an acid chloride in the presence of a base such as pyridine, triethylamine or aqueous sodium hydroxide. This acylation gives rise to the desired isomer 1b and the undesired isomer 3, which are separated by chromatography or crystallization. Compound 1b is oxidized to the aldehyde 1c by a reagent such as manganese dioxide. Mild acid or base hydrolysis of 1c gives 1d which is in equilibrium with lactol form 4. Alternatively, 1c can be oxidized with $Cr^{+6}$ reagents to acid 1e. Base treatment of 1e generates the salt 1f. Esters 1g can be prepared by reacting 1e with an alkylating agent in the presence of a base. The methyl ester of 1e is conveniently prepared on a small scale by the reaction of 1e with diazomethane in ether.

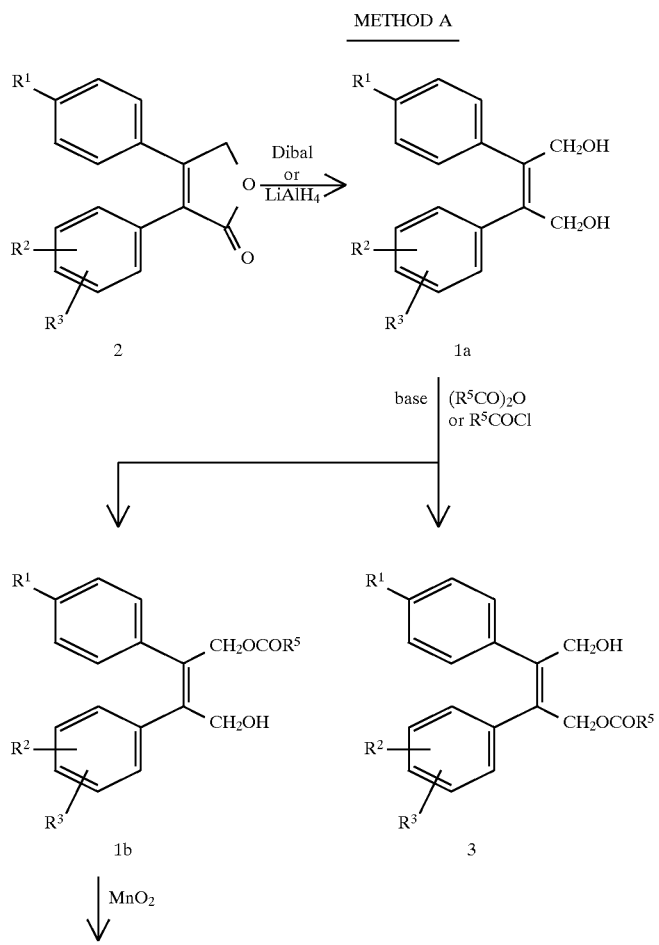

METHOD A

-continued
METHOD A
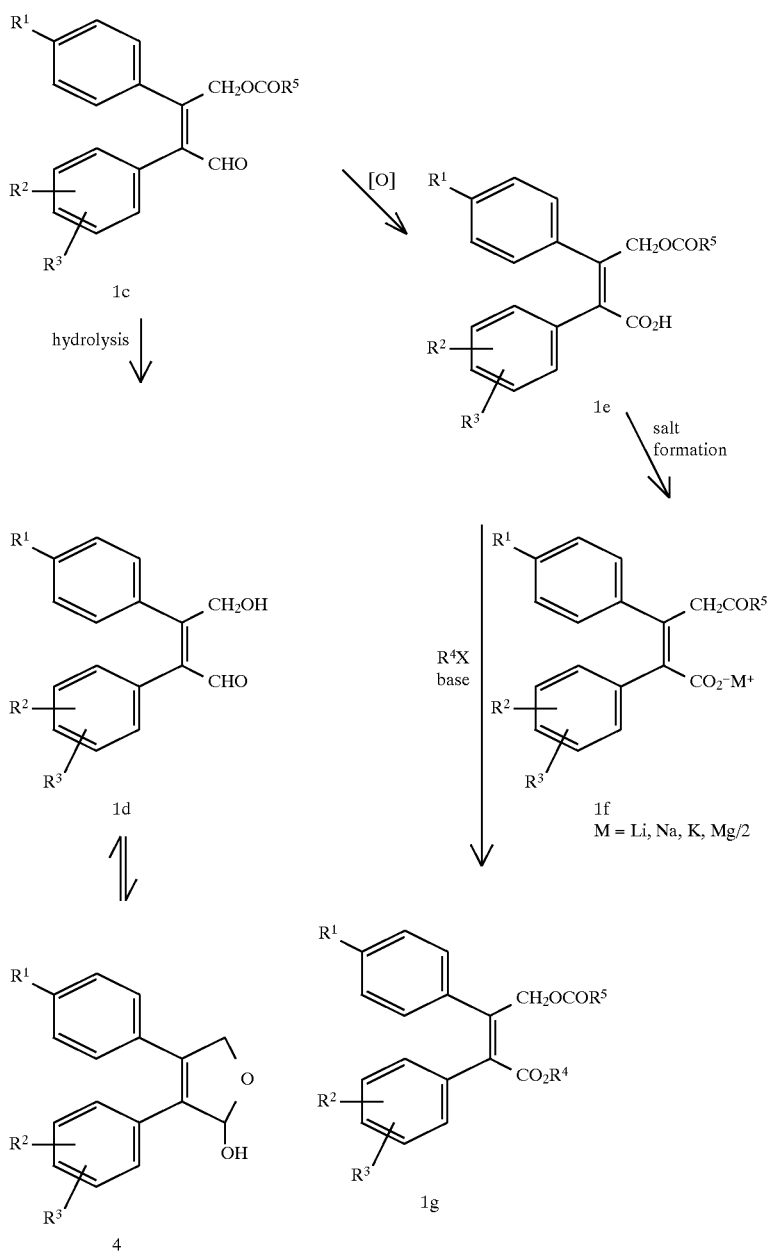
Method AA:
A diphenyl maleic anhydride 18 can be reduced to diol 1a with suitable hydride reducing agents such as di-isobutyl aluminum hydride or lithium aluminum hydride. Solvents such as toluene, tetrahydrofuran or ether, or a mixture thereof are suitable for the reduction.
METHOD AA
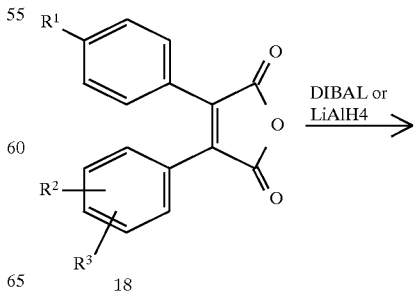

-continued
METHOD AA

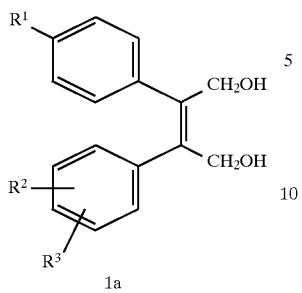

1a

METHOD C

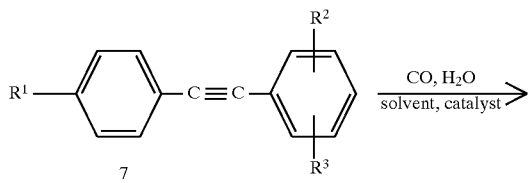

The lactones 2 are prepared by the following methods.

Method B:

An appropriately substituted aryl bromomethyl ketone 5 is reacted with an appropriately substituted aryl acetic acid 6 in a solvent such as acetonitrile in the presence of a base such as triethylamine and then treated with 1,8-diazabicyclo [5.4.0]undec-7-ene (DBU) to afford the lactone 2.

METHOD B

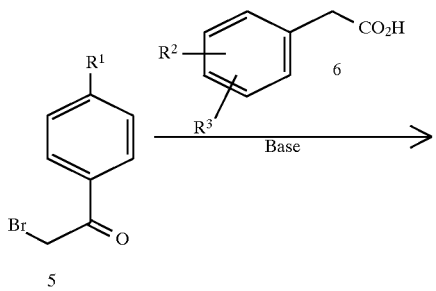

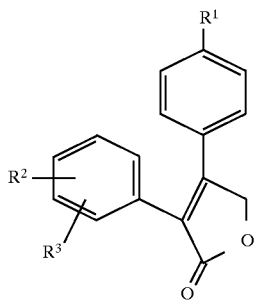

2

Method C

By reacting an acetylene 7 with carbon monoxide and water in the presence of suitable catalysts, a mixture of Compound 2 and its isomer 8 is obtained. The isomers are separable by standard procedures in the art such as chromatography or crystallization. Examples of useful catalysts and conditions are $PdCl_2$ in aqueous HCl and EtOH, heated at 50°–150° C. and 50–150 atmospheres of pressure, or $Rh_4(CO)_{12}$ (or $Rh_6(CO)_{16}$) in aqueous THF (or acetone, acetonitrile, benzene, toluene, EtOH, MeOH) containing a trialkylamine, at 50°–150° C. and 20–300 atmospheres pressure. See Takahashi et al., *Organomettallics* 1991, 10, 2493–2498; and Tsuji et al., *J. Am. Chem. Soc.* 1966, 88, 1289–1292.

Method D 1, 4-Addition to 9 of 4-methylthiophenyl organometallic reagents 10 in the presence of copper salts and the trapping of the resultant enolate with trialkyl silyl chloride such as TMSCl or TIPSCl provide the ketene acetal 11. The ketene acetal can then be oxidized to the substituted butenolide 12 by the method of Ito using catalytic amounts of $Pd_2(OAc)_2$ and $Cu(OAc)_2$ and $O_2$ in MeOH or by the method of Magnus using $PhIO/TMSN_3$ and $Bu_4NF$. Introduction of the iodine can be accomplished by treating 13 with $I_2$ in the presence of pyridine to afford 13. Palladium catalyzed Suzuki or Stille coupling of 13 with the appropriate aryl partner such as the boronic acid 14 provides the butenolide 15. The sulfide can be oxidized to a sulfone by various oxidizing agents such as peracetic acid, MPPM, MMPP or $H_2O_2$ to give the desired Compound 2a. See Y. Ito et al., *J. Am. Chem. Soc.* 1979, 101, 494, footnote 2, and P. Magnus et al., *Tet. Lett.* 1992, 2933.

METHOD D

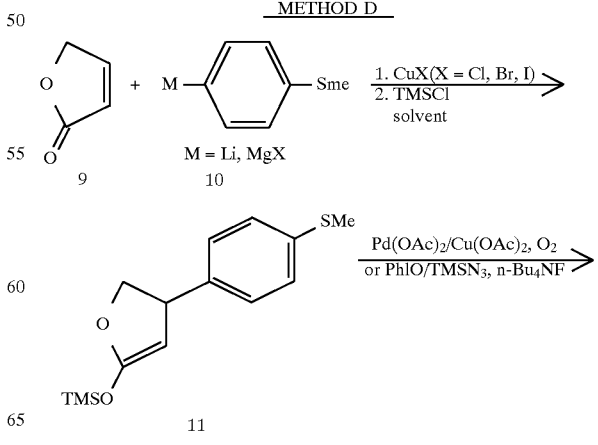

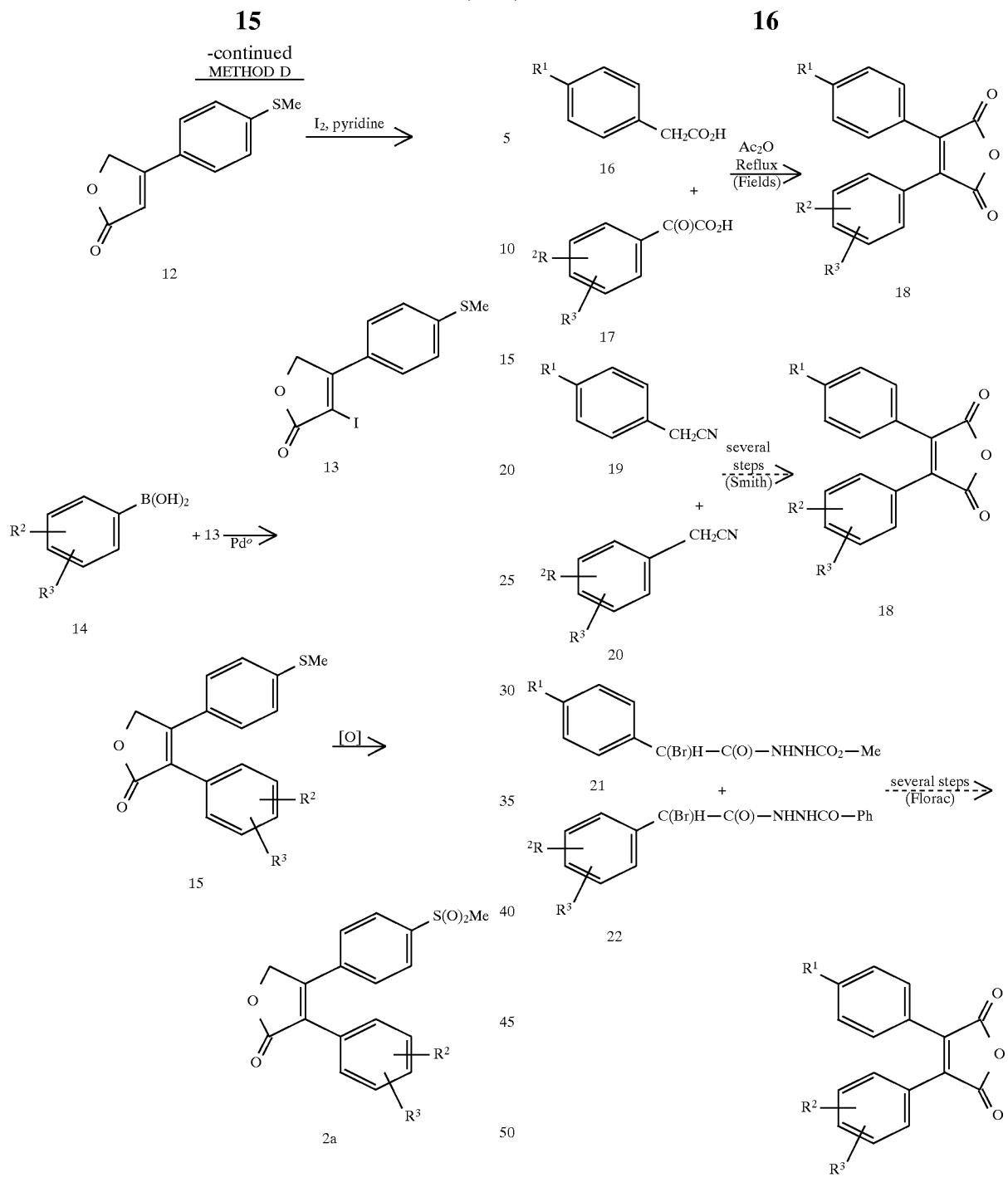

Representative Compounds

Method E

The 2,3-diphenyl maleic anhydride 18 can be prepared by the method of Fields [*J. Org. Chem.*, vol. 55, pp.5165–70 (1990); U.S. Pat. No. 4,596,867] in which a phenylacetic acid 16 is made to react with an α-oxophenylacetic acid 17 (preferably as its potassium salt) in refluxing acetic anhydride.

A multi-step sequence to 18 from phenylacetonitriles such as 19 and 20 is described by Smith, et. al., in *J. Org. Chem.*, vol. 55, pp. 3351–62 (1990).

Florac and co-workers in Tetrahedron, vol. 46, pp. 445–52 (1990) describe another synthesis of 18 in several steps from α-bromo phenylaceto hydrazides 21 and 22.

In Table I are shown some lactones 2 from which the compounds of the present invention can be prepared according to Method A.

In Table II and III are shown compounds representative of the present invention (structures Ia and Ib).

TABLE I

| Lactone | Structure |
|---|---|
| 1 | 3-phenyl-4-(4-(methylsulfonyl)phenyl)-2(5H)-furanone |
| 2 | 3-(4-fluorophenyl)-4-(4-(aminosulfonyl)phenyl)-2(5H)-furanone |
| 3 | 3-(2,4-difluorophenyl)-4-(4-(methylsulfonyl)phenyl)-2(5H)-furanone (ethyl) |
| 4 | 3-(3,4-difluorophenyl)-4-(4-(methylsulfonyl)phenyl)-2(5H)-furanone |
| 5 | 3-(2,6-difluorophenyl)-4-(4-(methylsulfonyl)phenyl)-2(5H)-furanone |
| 6 | 3-(2,5-difluorophenyl)-4-(4-(methylsulfonyl)phenyl)-2(5H)-furanone |

TABLE I-continued

| Lactone | Structure |
|---|---|
| 7 | 3-(3,5-difluorophenyl)-4-(4-(methylsulfonyl)phenyl) (ethyl) |
| 8 | 3-(4-bromophenyl)-4-(4-(methylsulfonyl)phenyl) (ethyl) |
| 9 | 3-(4-chlorophenyl)-4-(4-(methylsulfonyl)phenyl) (ethyl) |
| 10 | 3-(4-methoxyphenyl)-4-(4-(methylsulfonyl)phenyl) (ethyl) |
| 11 | 3-(4-fluorophenyl)-4-(4-(methylsulfonyl)phenyl) (ethyl) |
| 12 | 3-(2-chlorophenyl)-4-(4-(methylsulfonyl)phenyl) (ethyl) |

TABLE I-continued

| Structure | Lactone |
|---|---|
| 2-Br, 4-F phenyl / 4-S(O)₂Me phenyl lactone | 13 |
| 2-Br, 4-Cl phenyl / 4-S(O)₂Me phenyl lactone | 14 |
| 2-F, 4-Cl phenyl / 4-S(O)₂Me phenyl lactone | 15 |
| 4-F, 3-Br phenyl / 4-S(O)₂Me phenyl lactone | 16 |
| 3-Cl phenyl / 4-S(O)₂Me phenyl lactone | 17 |
| 2-Cl, 4-F phenyl / 4-S(O)₂Me phenyl lactone | 18 |
| 2-Cl, 4-Cl phenyl / 4-S(O)₂Me phenyl lactone | 19 |
| 3-Cl, 4-Cl phenyl / 4-S(O)₂Me phenyl lactone | 20 |
| 2-Cl, 6-Cl phenyl / 4-S(O)₂Me phenyl lactone | 21 |
| 4-F, 3-Cl phenyl / 4-S(O)₂Me phenyl lactone | 22 |
| 4-CF₃ phenyl / 4-S(O)₂Me phenyl lactone | 23 |
| 4-OMe, 3-F phenyl / 4-S(O)₂Me phenyl lactone | 24 |

TABLE I-continued

| Structure | Lactone |
|---|---|
| 3-Cl, 4-OMe phenyl / 4-S(O)₂Me phenyl lactone | 25 |
| 3-Br, 4-OMe phenyl / 4-S(O)₂Me phenyl lactone | 26 |
| 2-F phenyl / 4-S(O)₂Me phenyl lactone | 27 |
| 4-SMe phenyl / 4-S(O)₂Me phenyl lactone | 28 |
| 3-F phenyl / 4-S(O)₂Me phenyl lactone | 29 |
| 2-Cl, 3-F phenyl / 4-S(O)₂Me phenyl lactone | 30 |
| 3-Br, 4-Me phenyl / 4-S(O)₂Me phenyl lactone | 31 |
| 2-F, 4-Br phenyl / 4-S(O)₂Me phenyl lactone | 32 |
| 3,4-diBr phenyl / 4-S(O)₂Me phenyl lactone | 33 |
| 3-F, 4-Cl phenyl / 4-S(O)₂Me phenyl lactone | 34 |
| 3-F, 4-Br phenyl / 4-S(O)₂Me phenyl lactone | 35 |
| 2-Cl, 4-Br phenyl / 4-S(O)₂Me phenyl lactone | 36 |

TABLE I-continued

| Structure | Lactone |
|---|---|
| 3,4-dichlorophenyl / 4-(S(O)₂NH₂)phenyl lactone | 37 |
| 3,4-difluorophenyl / 4-(S(O)₂NH₂)phenyl lactone | 38 |
| 3-Cl-4-OMe-phenyl / 4-(S(O)₂NH₂)phenyl lactone | 39 |
| 3-Br-4-OMe-phenyl / 4-(S(O)₂NH₂)phenyl lactone | 40 |
| 4-(S(O)NH₂)phenyl / phenyl lactone | 41 |
| 4-F-phenyl / 4-(S(O)₂NH₂)phenyl lactone | 42 |
| 4-(S(O)₂NH₂)phenyl / 2,4-difluorophenyl ethyl lactone | 43 |
| 4-(S(O)₂NH₂)phenyl / 4-Cl-phenyl ethyl lactone | 44 |
| 4-(S(O)₂NH₂)phenyl / 2,4-dichlorophenyl ethyl lactone | 45 |
| 4-(S(O)₂NH₂)phenyl / 4-Br-phenyl ethyl lactone | 46 |
| 4-(S(O)₂NH₂)phenyl / 2-F-4-Br-phenyl ethyl lactone | 47 |

TABLE II

Ia (structure: Me-S(=O)(=O)-phenyl connected to C(X)=C(Y)-phenyl with R² and R³ substituents)

| Compound | R² | R³ | Y | X |
|---|---|---|---|---|
| 1 | H | H | CH₂OH | CH₂OH |
| 2 | H | H | CH₂OH | CH₂OAc |
| 3 | H | H | CHO | CH₂OAc |
| 4 | H | H | CO₂H | CH₂OAc |
| 5 | H | H | CO₂Me | CH₂OAc |
| 6 | H | H | CH₂OH | CH₂OCOPh |
| 7 | H | H | CHO | CH₂OCOPh |
| 8 | H | H | CO₂H | CH₂OCOPh |
| 9 | H | H | CO₂Me | CH₂OCOPh |
| 10 | F | F | CH₂OH | CH₂OH |
| 11 | F | F | CH₂OH | CH₂OAc |
| 12 | F | F | CHO | CH₂OAc |
| 13 | F | F | CO₂H | CH₂OAc |
| 14 | F | F | CO₂Me | CH₂OAc |
| 15 | H | F | CH₂OH | CH₂OH |
| 16 | H | F | CH₂OH | CH₂OAc |
| 17 | H | F | CHO | CH₂OAc |
| 18 | H | F | CO₂H | CH₂OAc |
| 19 | H | F | CO₂Me | CH₂OAc |

TABLE III

Ib (structure: H₂N-S(=O)(=O)-phenyl connected to C(X)=C(Y)-phenyl with R² and R³ substituents)

| Compound | R² | R³ | Y | X |
|---|---|---|---|---|
| 20 | H | H | CH₂OH | CH₂OH |
| 21 | H | H | CH₂OH | CH₂OAc |
| 22 | H | H | CHO | CH₂OAc |
| 23 | H | H | CO₂H | CH₂OAc |
| 24 | H | H | CO₂Me | CH₂OAc |
| 25 | H | H | CH₂OH | CH₂OCOPh |
| 26 | H | H | CHO | CH₂OCOPh |
| 27 | H | H | CO₂H | CH₂OCOPh |
| 28 | H | H | CO₂Me | CH₂OCOPh |
| 29 | F | F | CH₂OH | CH₂OH |
| 30 | F | F | CH₂OH | CH₂OAc |
| 31 | F | F | CHO | CH₂OAc |
| 32 | F | F | CO₂H | CH₂OAc |
| 33 | F | F | CO₂Me | CH₂OAc |
| 34 | H | F | CH₂OH | CH₂OH |
| 35 | H | F | CH₂OH | CH₂OAc |
| 36 | H | F | CHO | CH₂OAc |
| 37 | H | F | CO₂H | CH₂OAc |
| 38 | H | F | CO₂Me | CH₂OAc |

Assays for Determining Biological Activity

The compound of Formula I can be tested using the following assays to determine their cyclooxygenase-2 inhibiting activity.

Inhibition of Cyclooxygenase Activity

Compounds are tested as inhibitors of cyclooxygenase activity in whole cell and microsomal cyclooxygenase assays. Both of these assays measure prostaglandin $E_2$ ($PGE_2$) synthesis in response to arachidonic acid, using a radioimmunoassay. Cells used for whole cell assays, and from which microsomes are prepared for microsomal assays, are human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition. $IC_{50}$ values represent the concentration of putative inhibitor required to return $PGE_2$ synthesis to 50% of that obtained as compared to the uninhibited control.

Representative Rat Paw Edema Assay—Protocol

Male Sprague-Dawley rats (150–200 g) are fasted overnight and are given p.o., either vehicle (5% tween 80 or 1% methocell) or a test compound, at 9–10 a.m. One hr later, a line is drawn using a permanent marker at the level above the ankle in one hind paw to define the area of the paw to be monitored. The paw volume ($V_{oh}$) is measured using a plethysmometer (Ugo-Basile, Italy) based on the principle of water displacement. The animals are then injected subplantarly with 50 ul of a 1% carrageenan solution in saline (FMC Corp, Maine) into the paw using an insulin syringe with a 25-gauge needle (i.e. 500 ug carrageenan per paw). Three hr later, the paw volume ($V_{3h}$) is measured and the increases in paw volume ($V_{3h}-V_{oh}$) are calculated. The animals are euthanized by $CO_2$ aphyxiation and the absence or presence of stomach lesions scored. Stomach scores are expressed as the sum of total lesions in mm. Paw edema data are compared with the vehicle-control group and percent inhibition calculated taking the values in the control group as 100%. All treatment groups are coded to eliminate observer bias.

NSAID-Induced Gastropathy In Rats

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}$Cr excretion after systemic injection of $^{51}$Cr-labeled red blood cells. Fecal $^{51}$Cr excretion is a well-established and sensitive technique to detect gastrointestinal integrity in animals and man.

Methods

Male Sprague-Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}$Cr-labeled red blood cells from a donor rat. The animals are placed individually in metabolism cages with food and water ad lib. Feces are collected for a 48 hr period and $^{51}$Cr fecal excretion is calculated as a percent of total injected dose. $^{51}$Cr-labeled red blood cells are prepared using the following procedures. Ten mL of blood is collected in heparinized tubes via the vena cava from a donor rat. Plasma is removed by centrifugation and replenished with an equal volume of HBSS. The red blood cells are incubated with 400 μCi of sodium $^{51}$ chromate for 30 min. at 37° C. At the end of the incubation, the red blood cells are washed twice with 20 mL HBSS to remove free sodium $^{51}$ chromate. The red blood cells are finally reconstituted in 10 mL HBSS and 0.5 mL of the solution (about 20 μCi) is injected per rat.

Protein-Losing Gastrophathy in Squirrel Monkeys
Rationale

Protein-losing gastropathy (manifested as appearance of circulating cells and plasma proteins in the GI tract) is a significant and dose-limiting adverse response to NSAIDs. This can be quantitatively assessed by intravenous administration or $^{51}CrCl_3$ solution. This isotopic ion can avidly bind to cell and serum globins and cell endoplasmic reticulum. Measurement of radioactivity appearing in feces collected for 24 hr after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 μCi/kg in 1 ml/kg PBS) is administered 1 hr after the last drug/vehicle dose, and feces collected for 24 hr in a metabolism cage and assessed for excreted $^{51}Cr$ by gamma-counting. Venous blood is sampled 1 hr and 8 hr after the last drug dose, and plasma concentration of drug measured by RP-HPLC.

The invention will now be illustrated by the following non-limiting examples in which, unless stated otherwise:

(i) all operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

The following abbreviations have the indicated meanings:
Ac=acetyl
Bn=benzyl
DBU=1,8-diazabicyclo[5.4.0]undec-7-ene
DIBAL=diisobutylaluminum hydride
DMAP=4-(dimethylamino)pyridine
DMF =N,N-dimethylformamide
$Et_3N$=triethylamine
HBSS=Hanks' balanced salt solution
LDA=lithium diisopropylamide
m-CPBA=metachloroperbenzoic acid
MMPP=monoperoxyphtalic acid
MPPM=monoperoxyphthalic acid, magnesium salt $6H_2O$
Ms=methanesulfonyl=mesyl=$S(O)_2Me$
MsO=methanesulfonate=mesylate
NSAID=non-steroidal anti-inflammatory drug
OXONE®=$2KHSO_5.KHSO_4.K_2SO_4$
PBS=phosphate buffered saline
PCC=pyridinium chlorochromate
PDC=pyridinium dichromate
Ph=phenyl
Phe=benzenediyl
Pye=pyridinediyl
r.t.=room temperature
rac.=racemic
SAM=aminosulfonyl or sulfonamide or $S(O)_2NH_2$
TBAF=tetra-n-butylammonium fluoride
Th=2- or 3-thienyl
TFAA=trifluoroacetic acid anhydride
THF=tetrahydrofuran
Thi=thiophenediyl
TLC=thin layer chromatography
TMS-CN=trimethylsilyl cyanide
Tz=1H (or 2H)-tetrazol-5-yl
$C_3H_5$=allyl
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

EXAMPLE 1

(Z)-2-(4-(Methylsulfonyl)Phenyl)-3-Phenyl-2-Butene-1,4-Diol

To a solution of DIBAL (75 mL, 1 M in toluene) cooled to 0° C. was added dropwise a solution of Lactone 1 (5.0 g in 200 mL of THF). After stirring for 30 min at 0° C. and 30 min at r.t., the mixture was then transfered into 200 mL of 1M sodium potassium tartrate containing 50 mL of MeOH via a double-tipped needle. The product was extracted with EtOAc (200 mL) and dried over $MgSO_4$. Filtration and concentration provided the title compound (5.0 g) as a colorless syrup.

Alternative Preparation

To a mixture of 3.28 g (10 mmol) of anhydride 1 and 200 mL of $Et_2O$ is added 0.76 g (20 mmol) of $LiAlH_4$. The addition is done in portions over a period of 20 min while the reaction mixture is stirred vigorously at r.t. After an additional 30 min, 1N HCl is added, the layers are separated and the aqueous layer is extracted with 200 mL of $Et_2O$. The combined $Et_2O$ extracts are dried ($MgSO_4$), evaporated and the residue chromatographed to obtain the title compound.

EXAMPLE 2

(Z)-2-(4-(Methylsulfonyl)Phenyl)-3-Phenyl-2-Butene-1,4-Diol 1-Acetate

A solution of 2-(4-(methylsulfonyl)phenyl)-3-phenyl-2butene-1,4-diol (149 mg) and $Et_3N$ (0.2 mL) in 20 mL of CH$_2$Cl$_2$ was treated with Ac$_2$O (0.05 mL) and DMAP (5 mg). After stirring for 10 min at r.t., the mixture was concentrated, and the residue was purified by flash chromatography eluted with 3:2 EtOAc/hexane to afford 40 mg of the title compound as a white solid along with 30 mg of its regioisomer as a syrup.
$^1$NMR (acetone-d$_6$) δ7.70 (2H, d), 7.32 (2H, d), 7.05–7.12 (5H, m), 5.71 (2H, s), 4.62 (2H, d), 4.06 (1H, t), 3.05 (3H, s), 1.93 (3H, s).

EXAMPLE 3

(Z)-4-Acetoxy-3-(4-(Methylsulfonyl)Phenyl)-2-Phenyl -2-Butenal

A mixture of the acetate from Example 2 (215 mg) and MnO$_2$ (1.2 g) in 30 mL of CH$_2$Cl$_2$ was stirred for 12 h at r.t., and then filtered through a pad of celite. The filtrate was concentrated to give 160 mg of the title compound as a yellow solid.
$^1$NMR (acetone-d$_6$) δ10.50 (1H, s), 7.78 (2H, d), 7.46 (2H, d), 7.16 (3H, m), 6.98 (2H, m), 5.60 (2H, s), 3.06 (3H, s), 1.93 (3H, s).

EXAMPLE 4

(Z)-4-Acetoxy-3-(4-(Methylsulfonyl)Phenyl)-2-Phenyl -2-Butenoic Acid

To a solution of the aldehyde from Example 3 (160 mg) and 2-methyl-2-butene (6 mL) in 2-methyl-2-propanol (35 mL) was added a solution of NaClO$_2$ (1 g) and NaH$_2$PO$_4$ (1 g) in 10 mL of H$_2$O. The mixture was stirred for 2 h at r.t., and concentrated. The residue was then taken into 50 mL of pH 7 buffer solution (1M) and extracted with EtOAc (50 mL). The extract was dried over MgSO$_4$ and concentrated. The residue was purified by flash chromatography, eluting with 3:1 EtOAc/hexane containing 1% HOAc to give 150 mg of the title compound as a white solid.
$^1$NMR (acetone-d$_6$) δ7.77 (2H, d), 7.43 (2H, d), 7.10–7.20 (5H, m), 5.25 (2H, s), 3.06 (3H, s), 2.60–3.00 (1H, bs), 1.89 (3H, s).

EXAMPLE 5

(Z)-4-Acetoxy-3-(4-(Methylsulfonyl)Phenyl)-2-Phenyl-2-Butenoic Acid, Methyl Ester To a suspension of the acid from Example 4 (100 mg) in Et$_2$O (20 mL) was added dropwise excess CH$_2$N$_2$ solution in Et$_2$O. The solution was concentrated and the solid was swished with 2:1 hexane/EtOAc to give 90 mg of the title compound as a white solid.
$^1$NMR (acetone-d$_6$) δ7.79 (2H, d), 7.44 (2H, d), 7.17 (3H, m), 7.08 (2H, m), 5.17 (2H, s), 3.80 (3H, s), 3.06 (3H, s), 1.90 (3H, s).

PREPARATION OF MALEIC ANHYDRIDE INTERMEDIATES

ANHYDRIDE 1

2-(4-(Methylsulfonyl)Phenyl)-3-Phenylmaleic Anhydride

A mixture of 21.4 g (0.10 mol) of 4-(methylsulfonyl) phenylacetic acid [Forrest, et al., *J. Chem. Soc.* (1948), 1501–1506] and 18.8 g (0.10 mol) of potassium benzoyl formate in 200 mL of Ac$_2$O is stirred and refluxed for 2 h. The reaction mixture is cooled to r.t. and poured into 1L of H$_2$O and stirred until the Ac$_2$O dissolves (ca. 2h). The precipitate is filtered and dried to obtain the title compound. If desired, it is recrystallized from HOAc or acetone.

PREPARATION OF LACTONE INTERMEDIATES

LACTONE 1

Preparation A

3-Phenyl-4-(4-(Methylsulfonyl)Phenyl)-2-(5H)-Furanone

To a solution of phenylacetic acid (27.4 g, 201 mmol) and 2bromo-1-(4-(methylsulfonyl)phenyl)ethanone (Lactone 11, Step 1) (60 g, 216 mmol, 1.075 eq.) in acetonitrile (630 mL) at 25° C. was added slowly Et$_3$N (30.8 mL, 1.1 eq.). The mixture was stirred for 20 min. at r.t. and then cooled in an ice bath. DBU (60.1 mL, 3 eq.) was slowly added. After stirring for 20 min. in the ice bath, the reaction was complete and the mixture was acidified with 1N HCl (color changes from dark brown to yellow). Then 2.4 L of ice and H$_2$O were added, stirred for a few minutes, then the precipitate was filtered and rinsed with H$_2$O (giving 64 g of crude wet product). The solid was dissolved in 750 mL of CH$_2$Cl$_2$, dried over MgSO$_4$, filtered and 300 g of silica gel was added. The solvent was evaporated to near dryness (silica gel a bit sticky) and the residue was applied on top of a silica gel plug in a sintered glass funnel and eluted with 10% EtOAc/CH$_2$Cl$_2$, giving after evaporation of the solvent and a swish in EtOAc, 36.6 g (58%) of the title compound.

Analysis calculated for C$_{17}$H$_{14}$O$_4$S C, 64.95; H, 4.49; S, 10.20 Found: C, 64.63; H, 4.65; S, 10.44

Preparation B

3-Phenyl-4-(4-(Methylsulfonyl)Phenyl)-2-(5H)-Furanone

Into a 20 ml glass ampule are added 1 g of 2-(4-(methylsulfonyl)phenyl)phenylacetylene, 20 mg of Rh$_4$(CO)$_{12}$, 1.5 g of Et$_3$N, 10 mL of THF and 1 mL of H$_2$O under a nitrogen atmosphere, and the ampule is placed in a 100-ml stainless steel autoclave. The reaction system is flushed three times with CO then charged at r.t. to a initial CO pressure of 100 atm. The reaction is kept at 100° C. for 5 hr. The solution is then diluted with 50 mL of benzene and washed with brine and 1N HCl. The benzene solution is dried over Na$_2$SO$_4$, and concentrated. The crude products are separated by column chromatography on silica gel, eluting with 2:1 EtOAc/hexane to give the title compound and its regioisomer.

Preparation C

3-Phenyl-4-(4-(Methylsulfonyl)Phenyl)-2-(5H-Furanone

Step 1: 2-Trimethylsilyloxy-4-(4-(methylthio)phenyl)-3,4-dihydrofuran

To a solution of 3.86 g (19 mmol) of 4-bromothioanisole in 90 mL of Et$_2$O cooled at −78° C., is added 22 mL of 1.7M solution of t-BuLi in pentane (38 mmol) dropwise. The reaction mixture is stirred for 15 min. at −78° C. and 3.8 g of CuI is added and the reaction mixture is allowed to warm to -40° C. over a period of 30 min. A solution of 1.7 g of 2(5H)-furanone in 10 mL of THF is added. After stirring for 1 hr, 2 mL of freshly distilled TMSCl is added dropwise. The reaction mixture is then treated with 2 mL of Et₃N and 50 ml of sat. NaHCO₃, and extracted with 100 mL of Et₂O. The Et₂O layer is dried over Na₂SO₄ and concentrated to the crude title compound which is used for the next step without further purification.

Step 2: 4-(4-(Methylthio)phenyl)-2-(5H)-furanone

To a solution of 4 g of Pd(OAc)₂ in 100 ml of acetonitrile is added dropwise the crude product from Step 1 (5 g) under nitrogen at r.t.

After 10 hr at r.t., the mixture is concentrated by evaporation and the residue is purified by flash chromatography on silica gel eluted with 2:1 hexane/EtOAc to give the title compound.

Step 3: 3-Iodo-4-(4-(methylthio)phenyl)-2-(5H)-furanone

To a solution of 3 g of the product of Step 2 in 30 mL of pyridine is added 8.7 g of 12. The mixture is stirred for 24 hr and then diluted with 200 mL of Et₂O, washed with 100 mL of 5N HCl and 50 mL of 5N Na₂S₂O₃. The Et₂O layer is dried over Na₂SO₄ and concentrated to give the title compound.

Step 4: 3-Phenyl-4-(4-(methylthio)phenyl)-2-(5H)-furanone

A mixture of 4 g of the product of Step 3, 3.7 g of PhB(OH)₂, 0.4 g of Ph₃As, 0.4 g of PdCl₂(PhCN)₂ in 100 mL of benzene and 15 mL of 2N NaOH is refluxed for 6 hr. Et₂O (200 mL) is then added and the mixture is washed with 100 mL of saturated NaHCO₃. The organic layer is dried over MgSO₄ and concentrated. The residue is purified by flash chromatography on silica gel eluted with 4:1 hexane/EtOAc to give the title compound.

Step 5: 3-Phenyl-4-(4-(methylsulfonyl)phenyl)-2-(5H)-furanone

To a solution of 3 g of the product of Step 4 in 80 mL of 10:1 CH₂Cl₂/MeOH is added 5.5 g of MPPM. The reaction mixture is stirred at r.t. for 2 hr and then diluted with 100 mL of 1:1 hexane/EtOAc. After filtration and concentration, the residue is purified by flash chromatography eluted with 2:1 EtOAc/hexane to give the title product.

LACTONE 2

3-(4-Fluorophenyl)-4-(4-(Aminosulfonyl)Phenyl)-2-(5H)-Furanone
$^1$H NMR (CD₃COCD₃) δ5.34 (2H, s), 6.67 (2H, bd), 7.18 (2H, m), 7.46 (2H, m), 7.61 (2H, m), 7.90 (2H, m). M.P. 187°–188° C.(d).

LACTONE 3

3-(2,4-Difluorophenyl)-4-(4-(Methylsulfonyl)Phenyl)-2-(5H)-Furanone

Analysis calculated for $C_{17}H_{12}F_2O_4S$ C, 58.28; H, 3.45; S, 9.15 Found: C, 58.27; H, 3.50; S, 9.27

LACTONE 4

3-(3,4-Difluorophenyl)-4-(4-(Methylsulfonyl)Phenyl)-2-(5H)-Furanone

To a solution of 3,4-difluorophenylacetic acid (ALDRICH CHEMICAL) (10 g) and 2-bromo-1-(4-(methylsulfonyl) phenyl)ethanone (Lactone 11, Step 1) (17.3 g) in acetonitrile (200 mL) at r.t. was added slowly Et₃N (20.2 mL). After 1 hr at r.t., the mixture was cooled in an ice bath and treated with 17.4 mL of DBU. After 2 hr at 0° C., the mixture was treated with 200 mL of 1N HCl and the product was extracted with EtOAc, dried over Na₂SO₄ and concentrated. The residue was applied on top of a silica gel plug in a sintered glass funnel, eluted with 75% EtOAc/hexane, giving after evaporation of the solvent and a swish in EtOAc, 10 g of the title compound.

Analysis calculated for $C_{17}H_{12}F_2O_4S$ C, 58.28; H, 3.45; S, 9.15 Found: C, 58.02; H, 3.51; S, 9.35

LACTONE 5

3-(2,6-Difluorophenyl)-4-(4-(Methylsulfonyl)Phenyl)-2-(5H)-Furanone

Analysis calculated for $C_{17}H_{12}F_2O_4S$ C, 58.28; H, 3.45; S, 9.15 Found: C, 58.18; H, 3.50; S, 9.44

LACTONE 6

3-(2,5-Difluorophenyl)-4-(4-(Methylsulfonyl)Phenyl)-2-(5H)-Furanone

Analysis calculated for $C_{17}H_{12}F_2O_4S$ C, 58.28; H, 3.45; S, 9.15 Found: C,58.89;H,3.51;S,9.11

LACTONE 7

3-(3,5-Difluorophenyl)-4-(4-(Methylsulfonyl)Phenyl)-2-(5H)-Furanone

Analysis calculated for $C_{17}H_{12}F_2O_4S$ C, 58.28; H, 3.45; S, 9.15 Found: C, 58.27; H, 3.62; S, 9.32

LACTONE 8

3-(4-Bromophenyl)-4-(4-(Methylsulfonyl)Phenyl)-2-(5H)-Furanone

Analysis calculated for $C_{17}H_{13}BrO_4S$ C, 51.94; H, 3.33; S, 8.16 Found: C, 51.76; H, 3.42; S, 8.21

LACTONE 9

3-(4-Chlorophenyl)-4-(4-(Methylsulfonyl)Phenyl)-2-(5H)-Furanone
$^1$H NMR (300 MHz, CDCl₃) δ7.93 (2H, d), 7.49 (2H, d), 7.35 (4H, m), 5.16 (2H, s), 3.06 (3H, s)

LACTONE 10

3-(4-Methoxyphenyl)-4-(4-(Methylsulfonyl)Phenyl)-2-(5H)-Furanone

Analysis calculated for $C_{18}H_{16}O_5S$ C, 62.78 H, 4.68; S, 9.31 Found: C, 62.75; H, 4.72; S, 9.39

LACTONE 11

3-(4-Fluorophenyl)-4-(4-(Methylsulfonyl)Phenyl)-2-(5H)-Furanone

Step 1: 2-Bromo-1-(4-(methylsulfonyl)phenyl) ethanone

To a solution of 197 g of 4-(methylthio)acetophenone (ref: *JACS*, 1952,74, p. 5475) in 700 mL of MeOH and 3500 mL of CH₂Cl₂ was added 881 g of MMPP over a period of 30 min. After 3 hr at r.t. the reaction mixture was filtered and the filtrate was washed with 2 L of saturated aqueous solution of NaHCO$_3$ and 1 L of brine. The aqueous phase was further extracted with 2 L of CH$_2$Cl$_2$. The combined extracts was dried over Na$_2$SO$_4$ concentrated to give 240 g of 4-(methylsulfonyl)acetophenone as a white solid.

To a cooled (−5° C.) solution of 174 g of 4-(methylsulfonyl)acetophenone in 2.5 L of CHCl$_3$ was added 20 mg of AlCl$_3$, followed by a solution of 40 mL of Br$_2$ in 300 mL CHCl$_3$. The reaction mixture was then treated with 1.5 L of H$_2$O and the CHCl$_3$ was separated. The aqueous layer was extracted with 1 L of EtOAc. The combined extracts were dried over Na$_2$SO$_4$ and concentrated. The crude product was recystallized from 50/50 EtOAc/hexane to give 210 g of the title compound as a white solid.

Step 2

To the product of Step 1 (216 mg) dissolved in acetonitrile (4 mL) was added Et$_3$N (0.26 mL), followed by 4-fluorophenylacetic acid (102 mg). After 1.5 hr at r.t., 0.23 mL of DBU was added. The reaction mixture was stirred for another 45 min. and then treated with 5 mL of 1N HCl. The product was extracted with EtOAc, dried over Na$_2$SO$_4$ and concentrated. The residue was purified by flash chromatography (40% EtOAc in hexane) to yield 150 mg of the title compound as a solid.
$^1$H NMR (CD$_3$COCD$_3$) δ3.15 (3H, s), 5.36 (3H, s), 7.18 (2H, J=8.9 Hz, t), 7.46 (2H, m), 7.7 (2H, J=8.65 Hz, d), 7.97 (2H, J=8.68, d).

LACTONE 12

3-(2-Chlorophenyl)-4-(4-(Methylsulfonyl)Phenyl)-2-(5H)-Furanone

Analysis calculated for C$_{17}$H$_{13}$ClO$_4$S C, 58.54; H, 3.76; S, 9.19 Found: C, 58.59; H, 3.80; S, 9.37

LACTONE 13

3-(2-Bromo-4-Fluorophenyl)-4-(4-(Methylsulfonyl)Phenyl)-2-(5H)-Furanone

Analysis calculated for C$_{17}$H$_{12}$BrFO$_4$S C, 49.75; H, 2.93 Found: C, 49.75; H, 3.01

LACTONE 14

3-(2-Bromo-4-Chlorophenyl)-4-(4-(Methylsulfonyl)Phenyl)-2-(5H)-Furanone
$^1$H NMR (300 MHz, acetone-d$_6$) δ7.95 (2H, d), 7.85 (1H, d), 7.63 (2H, dd), 7.55 (1H, dd), 7.45 (1H, d), 5.50 (2H, s), 3.15 (3H, s)

LACTONE 15

3-(4-Chloro-2-Fluorophenyl)-4-(4-(Methylsulfonyl)Phenyl)-2-(5H)-Furanone
$^1$H NMR (300 MHz, acetone-d$_6$) δ8.0 (2H, d), 7.70 (2H, d), 7.50–7.30 (3H, m), 5.35 (2H, s), 3.15 (3H, s)

LACTONE 16

3-(3-Bromo-4-Fluorophenyl)-4-(4-(Methylsulfonyl)Phenyl)-2-(5H)-Furanone

Analysis calculated for C$_{17}$H$_{12}$BrFO$_4$S C, 49.75; H, 2.93 Found: C, 49.44; H, 2.98

LACTONE 17

3-(3-Chlorophenyl)-4-(4-(Methylsulfonyl)Phenyl)-2-(5H)-Furanone

Analysis calculated for C$_{17}$H$_{13}$ClO$_4$S C, 58.54; H, 3.76 Found: C, 58.29; H, 3.76

LACTONE 18

3-(2-Chloro-4-Fluorophenyl)-4-(4-(Methylsulfonyl)Phenyl)-2-(5H)-Furanone

Analysis calculated for C$_{17}$H$_{12}$ClFO$_4$S C, 55.67; H, 3.30 Found: C, 55.67; H, 3.26

LACTONE 19

3-(2,4-Dichlorophenyl)-4-(4-(Methylsulfonyl)Phenyl)-2-(5H)-Furanone

Analysis calculated for C$_{17}$H$_{12}$Cl$_2$O$_4$S C, 53.28; H, 3.16; S, 8.37 Found: C, 52.89; H, 3.23; S, 8.58

LACTONE 20

3-(3,4-Dichlorophenyl)-4-(4-(Methylsulfonyl)Phenyl)-2-(5H)-Furanone

Analysis calculated for C$_{17}$H$_{12}$Cl$_2$O$_4$S C, 53.28; H, 3.16; S, 8.37 Found: C, 53.07; H, 3.32; S, 8.51

LACTONE 21

3-(2,6-Dichlorophenyl)-4-(4-(Methylsulfonyl)Phenyl)-2-(5H)-Furanone

Analysis calculated for C$_{17}$H$_{12}$Cl$_2$O$_4$S C, 53.28; H, 3.16; S, 8.37 Found: C, 52.99; H, 3.22; S, 8.54

LACTONE 22

3-(3-Chloro-4-Fluorophenyl)-4-(4-(Methylsulfonyl)Phenyl)-2-(5H)-Furanone
$^1$H NMR (300 MHz, acetone-d$_6$) δ8.0 (2H, d), 7.70 (2H, d), 7.60 (1H, d), 7.25–7.40 (2H, m), 5.35 (2H, s), 3.15 (3H, s)

LACTONE 23

3-(4-Trifluoromethylphenyl)-4-(4-(Methylsulfonyl)Phenyl)-2-(5H)-Furanone
$^1$H NMR (CD$_3$COCD$_3$) δ8.10 (2H, d), 7.82–7.93 (4H, m), 7.75 (2H, d), 5.55 (2H, s), 3.30 (3H, s)

LACTONE 24

3-(3-Fluoro-4-Methoxyphenyl)-4-(4-(Methylsulfonyl)Phenyl)-2-(5H)-Furanone

Analysis calculated for C$_{18}$H$_{15}$FO$_5$S C, 59.66; H, 4.17 Found: C, 59.92; H, 4.37

LACTONE 25

3-(3-Chloro-4-Methoxyphenyl)-4-(4-(Methylsulfonyl)Phenyl)-2-(5H)-Furanone

Analysis calculated for C$_{18}$H$_{15}$ClO$_5$S C, 57.07; H, 3.99 Found: C, 57.29; H, 4.15

LACTONE 26

3-(3-Bromo-4-Methoxyphenyl)-4-(4-(Methylsulfonyl)Phenyl)-2-(5H)-Furanone

Analysis calculated for C$_{18}$H$_{15}$BrO$_5$S C, 51.08; H, 3.57 Found: C, 51.38; H, 3.62

LACTONE 27

3-(2-Fluorophenyl)-4-(4-(Methylsulfonyl)Phenyl)-2-(5H)-Furanone

Analysis calculated for $C_{17}H_{13}FO_4S$ C,61.44;H, 3.94 Found: C, 61.13; H, 3.85

LACTONE 28

3-(4-Methylthiophenyl)-4-(4-(Methylsulfonyl)Phenyl)-2-(5H)-Furanone $^1$H NMR (300 MHz, acetone-$d_6$) δ8.0 (2H, d), 7.70 (2H, d), 7.35 (2H, d), 7.25 (2H, d), 5.35 (2H, s), 3.15 (3H, s), 2.55 (3H, s)

LACTONE 29

3-(3-Fluorophenyl)-4-(4-(Methylsulfonyl)Phenyl)-2-(5H)-Furanone $^1$H NMR (300 MHz, $CDCl_3$) δ7.93 (2H, d), 7.49 (2H, d), 7.35 (1H, m), 7.12 (3H, m), 5.18 (2H, s), 3.06 (3H, s)

LACTONE 30

3-(2-Chloro-6-Fluorophenyl)-4-(4-(Methylsulfonyl)Phenyl)-2-(5H)-Furanone $^1$H NMR (300 MHz, acetone-$d_6$) δ8.0 (2H, d), 7.70 (2H, d), 7.55–7.65 (1H, m), 7.40 (1H, d), 7.30 (1H, m), 5.60 (2H, s), 3.15 (3H, s)

LACTONE 31

3-(3-Bromo-4-Methylphenyl)-4-(4-(Methylsulfonyl)Phenyl)-2-(5H)-Furanone

Analysis calculated for $C_{18}H_{15}BrO_4S$ C, 53.08; H, 3.71 Found: C,53.06;H, 3.83

LACTONE 32

3-(4-Bromo-2-Fluorophenyl)-4-(4-(Methylsulfonyl)Phenyl)-2-(SH)-Furanone

Analysis calculated for $C_{17}H_{12}BrFO_4S$ C, 49.65; H, 2.94 Found: C, 49.76; H, 3.00

LACTONE 33

3-(3,4-Dibromophenyl)-4-(4-(Methylsulfonyl)Phenyl)-2-(5H)-Furanone
1H NMR (300 MHz, acetone-$d_6$) δ8.0 (2H, d), 7.80 (1H, d), 7.75 (3H, m), 7.25 (1H, d), 5.35 (2H, s), 3.15 (5H, s)

LACTONE 34

3-(4-Chloro-3-Fluorophenyl)-4-(4-(Methylsulfonyl)Phenyl)-2-(SH)-Furanone

Analysis calculated for $C_{17}H_{12}ClFO_4S$ C, 55.67; H, 3.30 Found: C, 55.45; H, 3.30

LACTONE 35

3-(4-Bromo-3-Fluorophenyl)-4-(4-(Methylsulfonyl)Phenyl)-2-(5H)-Furanone

Analysis calculated for $C_{17}H_{12}BrFO_4S$ C, 49.66; H, 2.94; S, 7.80 Found: C, 49.79; H, 3.01; S, 7.51

LACTONE 36

3-(4-Bromo-2-Chlorophenyl)-4-(4-(Methylsulfonyl)Phenyl)-2-(SH)-Furanone

Analysis calculated for $C_{17}H_{12}BrClO_4S$ C, 47.74; H, 2.83; S, 7.50 Found: C, 47.92; H, 2.84; S, 7.42

LACTONE 37

3-(3,4-Dichlorophenyl)-4-(4-(Aminosulfonyl)Phenyl)-2-(5H)-Furanone $^1$H NMR (400 MHz, $CD_3COCD_3$) δ7.92 (2H, dd), 7,64 (3H, dm), 7.60 (1H, dd), 7.32 (1H, dd), 6.70 (1H, bs), 5.38 (2H, s)

LACTONE 38

3-(3 4-Difluorophenyl)-4-(4-(Aminosulfonyl)Phenyl)-2-(5H)-Furanone $^1$H NMR (400 MHz, $CD_3COCD_3$) δ7.92 (2H, dd), 7,64 (2H, dd), 7.30–7.45 (2H, m), 7.22 (1H, m), 6.68 (2H, bs), 5.37 (2H, s)

LACTONE 39

3-(3-Chloro-4-Methoxyphenyl)-4-(4-(Aminosulfonyl)Phenyl)-2-(5H)-Furanone

Analysis calculated for $C_{17}H_{14}ClNO_5S$ C, 53.76; H, 3.72, N, 3.69 Found: C, 53.32; H, 3.84, N, 3.59 M.S. (DCI, $CH_4$) calculated for M+, 379 Found for M++1, 380

LACTONE 40

3-(3-Bromo-4-Methoxyphenyl)-4-(4-(Aminosulfonyl)Phenyl)-2-(5H)-Furanone

Analysis calculated for $C_{17}H_{14}BrNO_5S$ C, 48.13; H, 3.33, N, 3.30 Found: C, 48.26; H, 3.40, N, 3.28 M.S. (DCI, $CH_4$) calculated for M+, 423 Found for M++1, 424

EXAMPLE 6 (COMPOUND 10)

(Z)-2-(4-(Methylsulfonyl)Phenyl)-3-(3,4-Difluorophenyl)-2-Butene-1,4-Diol

A solution of DIBAL (185 mL, 1M in toluene) was added dropwise to a solution of Lactone 4 (20 g in 800 mL of THF) at 0° C. After stirring for 90 min at 0° C. and 18h at r.t., the mixture was recooled to 0° C. and 100 mL of 1M sodium potassium tartrate was added dropwise. The product was extracted with ethyl acetate (200 mL) and dried over $MgSO_4$. Filtration and concentration provided the title compound (20 g) as a colorless syrup.
$^1$H NMR (acetone-$d_6$) d 7.73 (2H, d), 7.38 (2H, d), 7.05 (2H, m), 6.85 (1H, m), 4.60 (4H, d), 4.10 (2H, br), 3.05 (3H, s).

EXAMPLE 7 (COMPOUND 11)

(Z)-2-(4-(Methylsulfonyl)Phenyl)-3-(3,4-Difluorophenyl)-2-Butene-1,4-Diol-1-Acetate A solution of acetyl chloride (4.8 g) in $CH_2Cl_2$ (10 mL) was added dropwise to a solution of the diol from Example 10 (21.6 g), $Et_3N$ (17.4 mL) and DMAP (1.0 g) in $CH_2Cl_2$ (2.0 L) at 0° C. After stirring for 15 min., 1N HCl (300 mL) was added and the organic layer separated, dried over $MgSO_4$ and concentrated. The residue was purified by flash chromatography using 1:1 EtOAc/toluene to afford 5.9 g of the title compound as a syrup followed by 5.9 g of its regioisomer also as a syrup.
$^1$NMR (acetone-$d_6$) d 7.75 (2H, d), 7.37 (2H, d), 7.10 (2H, m), 6.85 (1H, m), 5.18 (2H, s), 4.62 (2H, d), 4.15 (1H, t), 3.05 (3H, s), 1.93 (3H, s).

EXAMPLE 8 (COMPOUND 12)

(Z)-4-Acetoxy-3-(4-(Methylsulfonyl)Phenyl)-2-(3,4-Difluorophenyl)-2-Butenal

A mixture of the acetate from Example 11 (5.4 g) and $MnO_2$ (4.3 g) in EtOAc was stirred for 18 h at r.t. and then filtered through a pad of celite. The filtrate was concentrated to give 3.6 g of the title compound as a yellow syrup.
$^1$H NMR (acetone-$d_6$) d 10.52 (1H, s), 7.85 (2H, d), 7.52 (2H, d), 7.10 (2H, m), 6.78 (1H, m), 5.63 (2H, s), 3.05 (3H, s), 1.95 (3H, s).

EXAMPLE 9 (COMPOUND 13a)

(Z)-4-Acetoxy-3-(4-Methylsulfonyl)Phenyl)-2-(3, 4Difluorophenyl)-2-Butenoic Acid To a solution of the aldehyde from Example 12 (3.6 g), 2methyl-2-butene (36 mL), THF (54 mL), and t-BuOH (180 mL) was added a solution of $NaClO_2$ (7.3 g) and $NaH_2PO_4$ (8.6 g) in $H_2O$ (108 mL). The mixture was stirred for 1 h at r.t. The top organic layer was separated and concentrated. The residue was redissolved in EtOAc (50 mL), dried over $MgSO_4$, filtered and reconcentrated. The residue was purified by flash chromatography using 1:1 EtOAc/hexane containing 5% acetic acid to afford 1.3 g of the title compound, m.p. 133°–134° C.

Analysis calculated for $C_{19}H_{16}F_2SO_6$ C, 55.60; H, 3.92; F, 9.25; S, 7.81 Found: C, 55.31; H, 4.00; F, 8.86; S, 8.04

EXAMPLE 10 (COMPOUND 13b)

(Z)-4-Acetoxy-3-(4-(Methylsulfonyl)Phenyl)-2-(3,4-Difluorophenyl)-2-Butenoic Acid Sodium Salt A mixture of the acid from Example 13a (1.18 g), $NaHCO_3$ (243 mg) and $H_2O$ (75 mL) was sonnicated for 30 min. and filtered through a cintered funnel to obtain a clear solution. The solution was frozen and lyophilized to afford 1.1 g of the title compound as a white powder.
$^1$H NMR (DMSO-$d_6$) d 7.68 (2H, d), 7.28 (2H, d), 7.20 (1H, m), 7.10 (1H, m), 6.68 (1H, m), 5.08 (2H, s), 3.15 (3H, s), 1.85 (3H, s).

What is claimed is:
1. A compound of Formula I

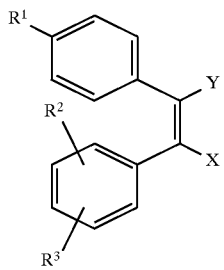

I or pharmaceutically acceptable salts thereof wherein
X is
(a) $CH_2OH$,
(b) CHO,
(c) $CO_2H$, or
(d) $CO_2R^4$;
Y is
(a) $CH_2OH$, or
(b) $CH_2OCOR^5$;
$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$;
$R^2$ and $R^3$ each are independently selected from the group consisting of
(a) hydrogen,
(b) halo,
(c) $C_{1-6}$alkoxy,
(d) $C_{1-6}$alkylthio,
(e) CN,
(f) $CF_3$,
(g) $C_{1-6}$alkyl,
(h) $N_3$;
$R^4$ is selected from the group consisting of
(a) hydrogen, and
(b) $C_{1-6}$alkyl;
$R^5$ is selected from the group consisting of
(a) hydrogen,
(b) $C_{1-6}$alkyl,
(c) mono- or disubstituted phenyl wherein the substituent is selected from
(1) hydrogen,
(2) halo,
(3) $C_{1-6}$alkyl,
(4) $C_{1-6}$alkoxy,
(5) $C_{1-6}$alkylthio,
(6) OH,
(7) CN,
(8) $CF_3$, and
(9) $CO_2R^4$,
with the proviso that the compound is other than 2-(4-fluorophenyl)-3-[(4-methylsulfonyl)phenyl]-1,4-dihydroxy-2-butene.

2. A compound according to claim 1
X is
(a) $CH_2OH$,
(b) CHO,
(c) $CO_2H$, or
(d) $CO2R^4$;
Y is
(a) $CH_2OH$, or
(b) $CH_2OCOR^5$;
$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$, and
(f) $S(O)(NH)NHC(O)CF_3$;
$R^2$ and $R^3$ each are independently selected from the group consisting of
(a) hydrogen,
(b) fluoro, chloro or bromo,
(c) $C_{1-4}$alkoxy,
(d) $C_{1-4}$alkylthio,
(e) CN,
(f) $CF_3$, and
(g) $C_{1-4}$alkyl;
$R^4$ is selected from the group consisting of
(a) hydrogen, and
(b) $C_{1-4}$alkyl,
$R^5$ is selected from the group consisting of
(a) hydrogen,
(b) $C_{1-4}$alkyl,
(c) mono- or disubstituted phenyl wherein the substituent is selected from
(1) hydrogen,
(2) halo, (3) $C_{1-6}$alky,
(4) $C_{1-6}$alkoxy,
(5) OH, and
(6) $CO_2R^4$.

3. A compound according to claim 2 wherein:
X is
 (a) $CH_2OH$,
 (b) CHO,
 (c) $CO_2H$, or
 (d) $CO_2R^4$;
Y is $CH_2OH$ or $CH_2OCOR^5$;
$R^1$ is selected from the group consisting of
 (a) $S(O)_2CH_3$,
 (b) $S(O)_2NH_2$,
 (c) $S(O)_2NHC(O)CF_3$,
 (d) $S(O)NHCH_3$,
 (e) $S(O)NHNH_2$, and
 (f) $S(O)NHNHC(O)CF_3$;
$R^2$ and $R^3$ are each independently selected from the group consisting of
 (1) hydrogen,
 (2) fluoro, chloro, and bromo,
 (3) $C_{1-4}$alkoxy,
 (4) $C_{1-4}$alkylthio,
 (5) CN,
 (6) $CF_3$,
 (7) $C_{1-4}$alkyl, and
 (8) $N_3$;
$R^4$ is selected from the group consisting of
 (a) hydrogen, and
 (b) $C_{1-4}$alky,
$R^5$ is selected from the group consisting of
 (a) hydrogen,
 (b) $C_{1-4}$alkyl,
 (c) mono- or disubstituted phenyl wherein the substituent is selected from
  (1) hydrogen,
  (2) halo,
  (3) $C_{1-6}$alky,
  (4) $C_{1-6}$alkoxy,
  (5) OH,
  (6) $CO_2R^4$.

4. A compound according to claim 3 wherein:
X is
 (a) $CH_2OH$,
 (b) CHO, or
 (c) $CO_2H$,
Y is $CH_2OH$ or $CH_2OCOR^5$;
$R^1$ is selected from the group consisting of
 (a) $S(O)_2CH_3$,
 (b) $S(O)_2NH_2$,
 (c) $S(O)NHCH_3$,
 (d) $S(O)NHNH_2$, and
$R^2$ and $R^3$ are each independently selected from the group consisting of
 (1) hydrogen, and
 (2) fluoro, chloro or bromo;
$R^4$ is hydrogen; and
$R^5$ is $C_{1-3}$alkyl.

5. A compound according to claim 4 wherein:
X is
 (a) $CH_2OH$,
 (b) CHO, or
 (c) $CO_2H$;
Y is $CH_2OH$ or $CH_2OCOR^5$;
$R^1$ is selected from the group consisting of
 (a) $S(O)_2CH_3$, and
 (b) $S(O)_2NH_2$,
$R^2$ and $R^3$ are each independently selected from the group consisting of
 (1) hydrogen,
 (2) fluoro, chloro or bromo;
$R^4$ is hydrogen; and
$R^5$ is $C_{1-3}$alkyl.

6. A compound according to claim 1 wherein:
X is $CO_2R^4$;
Y is $CH_2OCOR^5$,
$R^1$ is $S(O)_2CH^3$;
$R^2$ and $R^3$ each are independently selected from the group consisting of
 (a) hydrogen, and
 (b) halo;
$R^4$ is selected from the group consisting of
 (a) hydrogen, and
 (b) $C_{1-6}$alkyl;
$R^5$ is selected from the group consisting of
 (a) $C_{1-6}$alkyl, and
 (b) mono- or disubstituted phenyl wherein the substituent is selected from
  (1) hydrogen
  (2) halo
  (3) $C_{1-6}$alkoxy
  (4) OH.

7. A compound selected from the group consisting of
 (a) (Z)-2-(4-(methylsulfonyl)phenyl)-3-phenyl-2-butene-1,4-diol;
 (b) (Z)-2-(4-(methylsulfonyl)phenyl)-3-phenyl-2-butene-1,4-diol, 1-acetate;
 (c) (Z)-4-acetoxy-3-(4-(methylsulfonyl)phenyl)-2-phenyl-2-butenal;
 (d) (Z)-4-acetoxy-3-(4-(methylsulfonyl)phenyl)-2-phenyl-2-butenoic acid; and
 (e) (Z)-4-acetoxy-3-(4-(methylsulfonyl)phenyl)-2-phenyl-2-butenoic acid, methyl ester.

8. A compound of formula Ia

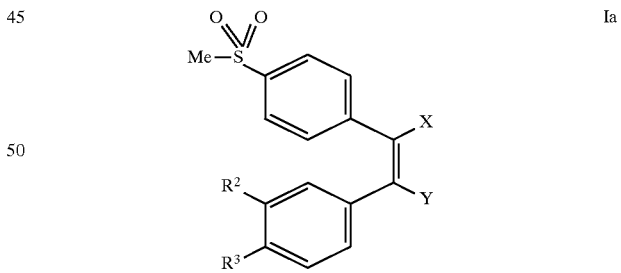

wherein the variables $R^2$, $R^3$, Y and X are selected from the following table:

| $R^2$ | $R^3$ | Y | X |
|---|---|---|---|
| H | H | $CH_2OH$ | $CH_2OH$ |
| H | H | $CH_2OH$ | $CH_2OAc$ |
| H | H | CHO | $CH_2OAc$ |
| H | H | $CO_2H$ | $CH_2OAc$ |
| H | H | $CO_2Me$ | $CH_2OAc$ |
| H | H | $CH_2OH$ | $CH_2OCOPh$ |
| H | H | CHO | $CH_2OCOPh$ |

-continued

| R² | R³ | Y | X |
|----|----|----|----|
| H | H | CO₂H | CH₂OCOPh |
| H | H | CO₂Me | CH₂OCOPh |
| F | F | CH₂OH | CH₂OH |
| F | F | CH₂OH | CH₂OAc |
| F | F | CHO | CH₂OAc |
| F | F | CO₂H | CH₂OAc |
| F | F | CO₂Me | CH₂OAc |
| H | F | CH₂OH | CH₂OH |
| H | F | CH₂OH | CH₂OAc |
| H | F | CHO | CH₂OAc |
| H | F | CO₂H | CH₂OAc |
| H | F | CO₂Me | CH₂OAc. |

9. A compound of formula Ib

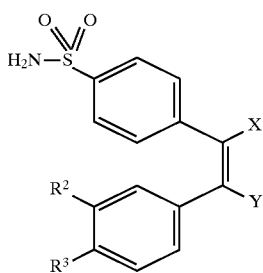

wherein the variables R², R³, X and Y are selected from the following table:

| R² | R³ | X | Y |
|----|----|----|----|
| H | H | CH₂OH | CH₂OH |
| H | H | CH₂OH | CH₂OAc |
| H | H | CHO | CH₂OAc |
| H | H | CO₂H | CH₂OAc |
| H | H | CO₂Me | CH₂OAc |
| H | H | CH₂OH | CH₂OCOPh |
| H | H | CHO | CH₂OCOPh |
| H | H | CO₂H | CH₂OCOPh |
| H | H | CO₂Me | CH₂OCOPh |
| F | F | CH₂OH | CH₂OH |
| F | F | CH₂OH | CH₂OAc |
| F | F | CHO | CH₂OAc |
| F | F | CO₂H | CH₂OAc |
| F | F | CO₂Me | CH₂OAc |
| H | F | CH₂OH | CH₂OH |
| H | F | CH₂OH | CH₂OAc |
| H | F | CHO | CH₂OAc |
| H | F | CO₂H | CH₂OAc |
| H | F | CO₂Me | CH₂OAc. |

10. A pharmaceutical composition for treating an inflammatory disease susceptible to treatment with a non-steroidal anti-inflammatory agent comprising:
  a non-toxic therapeutically effective amount of a compound according to claim 1, 2, 3, 4, 5 or 6 and a pharmaceutically acceptable carrier.

11. A pharmaceutical composition for treating cyclooxygenase mediated diseases advantageously treated by an active agent that selectively inhibits COX-2 in preference to COX-1 comprising:
  a non-toxic therapeutically effective amount of a compound according to claim 1, 2, 3, 4, 5 or 6 and a pharmaceutically acceptable carrier.

12. A method of treating an inflammatory disease susceptible to treatment with a non-steroidal anti-inflammatory agent comprising:
  administration to a patient in need of such treatment of a non-toxic therapeutically effective amount of a compound according to claim 1 and a pharmaceutically acceptable carrier.

13. A method of treating cyclooxygenase mediated diseases advantageously treated by an active agent that selectively inhibits COX-2 in preference to COX-1 comprising:
  administration to a patient in need of such treatment of a non-toxic therapeutically effective amount of a compound according to claim 1.

14. A compound according to claim 1 selected from the group consisting of:
  (a) (Z)-2-(4-(methylsulfonyl)phenyl)-3-(3,4-difluorophenyl)-2-butene-1,4-diol,
  (b) (Z)-2-(4-(methylsulfonyl)phenyl)-3-(3,4-difluorophenyl)-2-butene-1,4-diol, 1-acetate,
  (c) (Z)-4-acetoxy-3-(4-(methylsulfonyl)phenyl)-2-(3,4-difluorophenyl)-2-butenal,
  (d) (Z)-4-acetoxy-3-(4-(methylsulfonyl)phenyl)-2-(3,4-difluorophenyl)-2-butenoic acid, and
  (e) (Z)-4-acetoxy-3-(4-(methylsulfonyl)phenyl)-2-(3,4-difluorophenyl)-2-butenoic acid sodium salt.

15. A pharmaceutically acceptable salt of a compound of formula (I), as defined in claim 1, 2, 3, 4, 5 or 6.

16. A non-steroidal anti-inflammatory pharmaceutical composition comprising an acceptable anti-inflammatory amount of a compound of formula (I), as defined in claim 1, 2, 3, 4, 5 or 6, or a pharmaceutically accepatble salt thereof, in association with a pharmaceutically acceptable carrier.

17. A compound of formula (I), as defined in claim 1, 2, 3, 4, 5 or 6, or a pharmaceutically acceptable salt thereof, for use in the treatment of inflammatory disease susceptible to treatment with a non-steroidal anti-inflammatory agent.

* * * * *